(12) United States Patent
Vann, Jr.

(10) Patent No.: US 10,743,594 B2
(45) Date of Patent: Aug. 18, 2020

(54) ARM BANNER IDENTIFICATION SAFETY DEVICE

(71) Applicant: Raymond Kiah Vann, Jr., Lufkin, TX (US)

(72) Inventor: Raymond Kiah Vann, Jr., Lufkin, TX (US)

(*) Notice: Subject to any disclaimer, the term of this patent is extended or adjusted under 35 U.S.C. 154(b) by 146 days.

(21) Appl. No.: 16/002,600

(22) Filed: Jun. 7, 2018

(65) Prior Publication Data
US 2019/0373964 A1    Dec. 12, 2019

Related U.S. Application Data

(60) Provisional application No. 62/520,801, filed on Jun. 16, 2017.

(51) Int. Cl.
| | | |
|---|---|---|
| *A41D 13/00* | (2006.01) | |
| *A41D 13/01* | (2006.01) | |
| *A61F 5/058* | (2006.01) | |
| *A41D 13/08* | (2006.01) | |
| *A41D 19/015* | (2006.01) | |
| *A41D 20/00* | (2006.01) | |

(52) U.S. Cl.
CPC ............ *A41D 13/01* (2013.01); *A41D 13/08* (2013.01); *A41D 13/088* (2013.01); *A41D 19/0157* (2013.01); *A41D 20/00* (2013.01); *A61F 5/05858* (2013.01)

(58) Field of Classification Search
CPC ...... A41D 13/01; A41D 13/088; A41D 20/00; A41D 19/0157; A41D 13/08; A61F 5/05858
See application file for complete search history.

(56) References Cited

U.S. PATENT DOCUMENTS

| | | | | | |
|---|---|---|---|---|---|
| 1,762,549 | A | * | 6/1930 | Fisher | A41B 7/12 2/59 |
| 1,851,011 | A | * | 3/1932 | Jensen | A41D 13/08 2/16 |
| 3,837,007 | A | * | 9/1974 | Girest | A41D 27/10 359/519 |
| 4,856,112 | A | * | 8/1989 | Effle | A41D 13/08 2/59 |
| 4,884,297 | A | * | 12/1989 | Triche | A41D 13/08 2/16 |
| 5,737,771 | A | * | 4/1998 | Aanonsen | A41D 13/08 2/16 |
| 5,983,391 | A | * | 11/1999 | Palmer | A41D 13/08 2/16 |

(Continued)

OTHER PUBLICATIONS http://www.cherriescounterterror.com.
http://warrior-fire.com.
http://wasafety.com.au.

*Primary Examiner* — Khaled Annis
(74) *Attorney, Agent, or Firm* — Chen-Chi Lin

(57) ABSTRACT

An arm banner identification safety device and methods of use are presented. Embodiments include a flexible material banner with an exterior surface. Wording or lettering and/or symbols identifying an organization, organization type, occupation, and/or position is displayed on some part of the exterior banner. The banner is designed to be worn on the forearm, is held in place by use of adjustable straps, and can be easily folded to be kept in a pocket or purse.

6 Claims, 13 Drawing Sheets

(56) References Cited

U.S. PATENT DOCUMENTS

| | | | | |
|---|---|---|---|---|
| 6,128,777 | A * | 10/2000 | Foreman | A41D 13/08 128/878 |
| 6,374,408 | B1 * | 4/2002 | Tomlinson | A41D 13/0568 2/16 |
| 6,405,381 | B1 * | 6/2002 | Bowman, Jr. | A41D 19/0051 2/159 |
| 6,813,779 | B1 * | 11/2004 | Williams | A41D 13/08 2/16 |
| 6,931,666 | B1 * | 8/2005 | Brady | A41D 13/08 2/16 |
| 7,985,144 | B1 * | 7/2011 | Gonzales | A41D 13/0015 2/93 |
| 8,126,143 | B2 * | 2/2012 | Daniel | A63B 71/06 380/239 |
| 8,356,737 | B2 | 1/2013 | Lessman | |
| 8,387,294 | B2 | 3/2013 | Bolden | |
| 9,412,285 | B2 | 8/2016 | Ramirez | |
| 9,443,418 | B1 | 9/2016 | D'Orazio | |
| 9,854,901 | B2 | 1/2018 | Seuk | |
| 2006/0026730 | A1 * | 2/2006 | Terczak | A41D 13/08 2/59 |
| 2007/0118943 | A1 * | 5/2007 | Stockhamer | A41D 1/04 2/1 |
| 2009/0151045 | A1 * | 6/2009 | Hinds | A41D 20/00 2/170 |
| 2010/0083415 | A1 * | 4/2010 | Beckford | A41D 13/08 2/16 |
| 2011/0167536 | A1 * | 7/2011 | Kellerhals | A41D 20/00 2/170 |
| 2013/0047319 | A1 * | 2/2013 | Canale | A41D 20/00 2/243.1 |
| 2013/0104275 | A1 * | 5/2013 | Lea | A41D 13/08 2/16 |
| 2014/0121627 | A1 * | 5/2014 | Lepore | A61F 13/00 604/385.01 |
| 2016/0128859 | A1 * | 5/2016 | Brandt | A61F 5/0118 602/63 |
| 2016/0135522 | A1 * | 5/2016 | Rothschild | A41D 13/08 2/170 |
| 2016/0353813 | A1 * | 12/2016 | Rae | A41D 13/01 |
| 2016/0366954 | A1 * | 12/2016 | Barkshire | A41D 13/01 |
| 2017/0216078 | A1 * | 8/2017 | Rivlin | A61F 5/05866 |
| 2017/0340039 | A1 * | 11/2017 | Jur | A41D 13/0512 |
| 2018/0008449 | A1 * | 1/2018 | Feinstein | A61F 5/058 |
| 2018/0092791 | A1 * | 4/2018 | Alper | A61H 1/008 |
| 2018/0295903 | A1 * | 10/2018 | Yuan | A41D 1/002 |
| 2019/0029340 | A1 * | 1/2019 | Aguilar | A41D 13/08 |
| 2019/0142087 | A1 * | 5/2019 | Kelly | A41D 20/00 2/170 |

\* cited by examiner

ARM BANNER IDENTIFICATION SAFETY DEVICE

CROSS-REFERENCE TO RELATED PATENT APPLICATIONS

This patent application is intended to claim the benefit of U.S. provisional patent application Ser. No. 62/520,801 filed Jun. 16, 2017. The 62/520,801 application is hereby incorporated by reference into this application.

BACKGROUND OF THE INVENTION

The present invention relates generally to equipment for safety and more specifically it relates to an identification safety device made of flexible material with identifying wording or lettering and/or symbols and reflective attributes, that folds small enough to be carried on the person, and is to be worn on the forearm attached by adjustable straps and used by first responders including law enforcement officers, emergency medical service providers, firefighters and others, as well as other individuals authorized to carry and/or use a firearm, who are in plainclothes and cannot be identified by uniform.

When first responders including law enforcement officers, emergency medical service providers and firefighters, as well as other individuals licensed or authorized to carry a firearm, are not wearing a uniform but are wearing plainclothes and respond to an active shooter incident or other similar emergency incident, it is very difficult for other first responders and individuals to recognize the plainclothes first responders as being there to help. Without clearly visible identification, the plainclothes first responders, especially if armed, can be mistaken for the active shooter or other threatening suspect. This lack of identification associated with plainclothes first responders poses a very real threat to their safety and the safety of others since they are at risk of having deadly forced mistakenly used against them by other first responders or individuals who do not recognize them as plainclothes first responders.

The current practice of plainclothes first responders, especially law enforcement officers, in identifying themselves while responding to active incidents such as active shooter incidents, is to place a department or agency badge on a chain hanging around their neck, on their belt, or in their hand. This practice is an unreliable practice as the badge is difficult to see due to its small size and placement on the body. For example, a badge worn on a chain around the neck can only be seen by another person who is close enough to see it and who is located directly in front of the plainclothes first responder wearing the badge. Other persons who are further away or at a side angle, or behind the plainclothes first responder wearing the badge will not be able to see the badge unless the plainclothes first responder turns his/her torso toward the other person or unless the plainclothes first responder somehow lifts the badge at an angle for the person to see. Lifting the badge at a proper angle is often impossible due to the short chain and/or position of the person. This practice is also unsafe because in order to allow the other person to see the badge, in many cases, the plainclothes first responder would need to advance closer to the other person, turn their torso towards the other person, and/or raise the badge toward the other person. All three of these actions, especially if the plainclothes first responder is armed, can be mistaken for aggressive action toward the other person which may result in the other person mistakenly using deadly force against the plainclothes first responder.

Any discussion of the prior or related art throughout the specification should in no way be considered as an admission that such prior art is widely known or forms part of common general knowledge in the field.

Other items are available to help identify plainclothes first responders. Most notable are outer vests and jackets that identify the plainclothes first responder. However, these items are not always accessible and are usually not carried on the person of the plainclothes first responder. If an incident unfolds while the plainclothes first responder is off-duty and in a public space, that plainclothes first responder will most likely not have an identifying vest or other outer garment with them.

There are other devices, such as vests, badge holders, hats, and full body banners, which exist and are used for a similar purpose as the present invention, but they are not worn on the forearm, can be slow to deploy, require a training system, and/or are not as convenient for the user to carry because they often require a pouch or bag for carrying when not in use. Being worn on the arm is important because it allows the user to easily show others the banner identifying them without making threatening or aggressive movements.

Examples of patented safety devices which are illustrative of such prior art include U.S. Pat. No. 9,443,418 to D'Orazio; U.S. Pat. No. 9,412,285 Ramirez; U.S. Pat. No. 9,854,901 Seuk; U.S. Pat. No. 8,387,294 to Bolden; U.S. Pat. No. 8,356,737 to Lessman.

Although these patented devices serve a similar purpose as the present invention, two require electronic lights, two require a law enforcement badge, and one is worn across the torso. Of the two worn on the wrist, one requires an electronic light system and it requires training of other first responders to understand the communication of the light system. The other one worn on the wrist requires a law enforcement badge and is not as visible as the present invention. The prior art worn across the torso serves a similar purpose as the present invention, but is not worn on the forearm, and requires a pouch in ordered to be carried. Because it is worn on the torso, it limits the wearers ability to display the intended identification in any direction.

Other examples of prior art are the Israeli Style Pocket Carry Police Hat (website: cherriescounterterror.com), and other armbands worn on the upper arm (websites: warriorfire.com and wasafety.com). The Israeli Style Pocket Carry Police Hat also serves a similar purpose as the present invention, but it is worn on the head. Armbands worn on the upper arm can only be seen by those located on same side of the arm wearing the armband and since it is located on the upper arm, the wearer cannot maneuver it in a way to be seen by others located at other positions. In addition, these armbands are not easily worn by persons who are wearing outer garments.

While these prior art examples may serve the purpose of helping identify first responders including law enforcement officers, emergency medical service providers and firefighters, as well as other individuals licensed or authorized to carry a firearm, none combine the important qualities of 1) the ease of carry by folding in order to be carried in a pocket or purse, 2) the maximum maneuverability associated with a device worn on the forearm, 3) the high visibility associated with using materials that are bright, reflective, and/or contrasting, and 4) ease of deployment associated with using adjustable straps to attach.

BRIEF SUMMARY OF THE INVENTION

The present invention is an identification safety device to be worn by first responders including law enforcement officers, emergency medical service providers and firefighters, as well as other individuals licensed or authorized to carry a firearm, who are in plainclothes and cannot be identified or recognized by uniform. The present invention is highly visible and designed to assist uniformed law enforcement officers, as well as others, in quickly recognizing other first responders wearing plainclothes, as well as individuals who are legally armed and may be assisting in an active incident or other situation.

The present invention is an identification safety device is designed to be worn on the forearm, that is highly visible and easily recognizable and that can be easily folded to be kept in a pocket or purse. It is designed with bright and/or contrasting materials and uses reflective materials to produce high visibility with wording or lettering for quick recognition. The present invention is unique because it is worn on the forearm and held in place by use of adjustable straps. It is also unique because it is designed in a manner that allows folding to the size or smaller than a standard wallet. This allows the user to carry it every day and everywhere with minimal inconvenience.

A primary object of the present invention is to provide an identification safety device for first responders including law enforcement officers, emergency medical service providers and firefighters, as well as other individuals licensed or authorized to carry a firearm that will overcome the shortcomings of the prior art devices.

A second object is to provide an identification safety device that can be folded and carried at all times regardless of dress so that the user can always have it with him/her.

Another object is to provide an identification safety device that can be worn on the forearm where it can be easily maneuvered to be shown to others at any angle.

An additional object is to provide an identification safety device that is held on the arm using adjustable straps so that it can be adjusted to be worn on the forearm regardless of clothing thickness or layering.

A further object is to provide an identification safety device that is visible enough to be seen from a distance, which includes bright and/or contrasting materials A further object is to provide an identification safety device that has reflective qualities so that it can be seen in most low light conditions.

A further object is to provide an identification safety device that has identifying wording, acronyms, and/or symbols for quick recognition.

Other objects and advantages of the invention will appear as the description proceeds and will become obvious to the reader. It is intended that these other objects and advantages are within the scope of the present invention.

To the accomplishment of the above and related objects, this present invention may be embodied in the form illustrated in the accompanying drawings, however, attention being called to the fact that the drawings are illustrative only, and that changes may be made in the specific construction illustrated and described within the scope of the appended claims.

BRIEF DESCRIPTION OF THE DRAWINGS AND PHOTOGRAPHS

Various other objects, features and attendant advantages of the present invention will become fully appreciated as the same becomes better understood when considered in conjunction with the accompanying drawings, in which like reference characters designate the same or similar parts throughout the sever views, and wherein.

Figure 1:
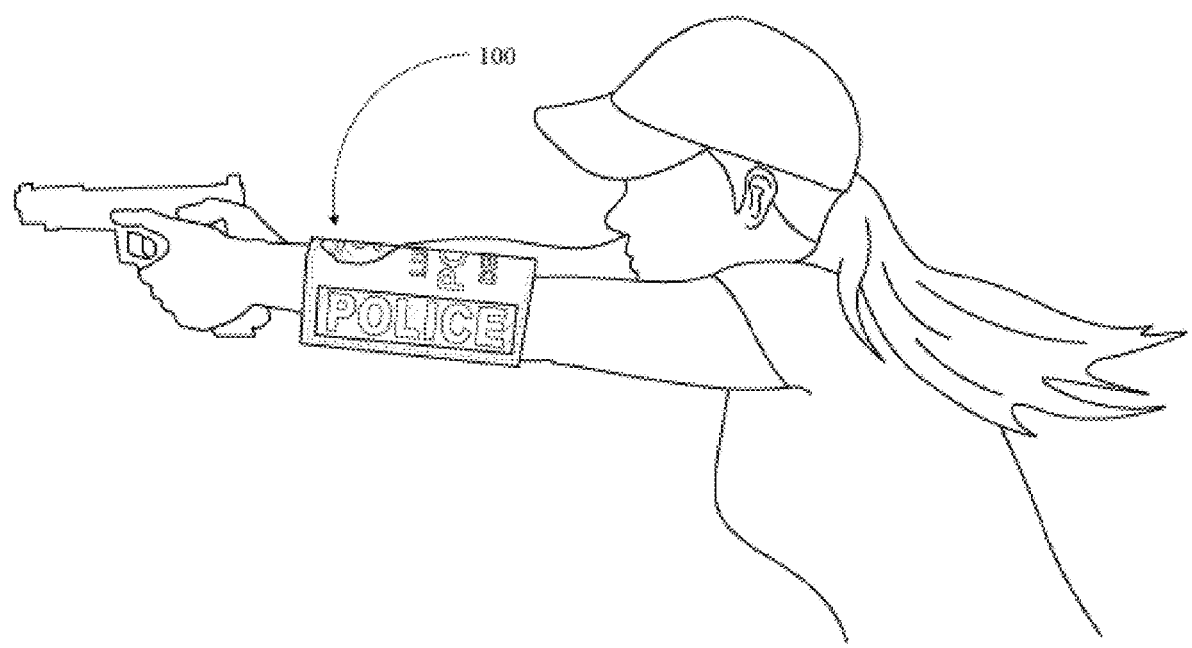
FIG. 1 depicts a perspective view of an arm banner identification safety device of the present invention.
Figure 9:
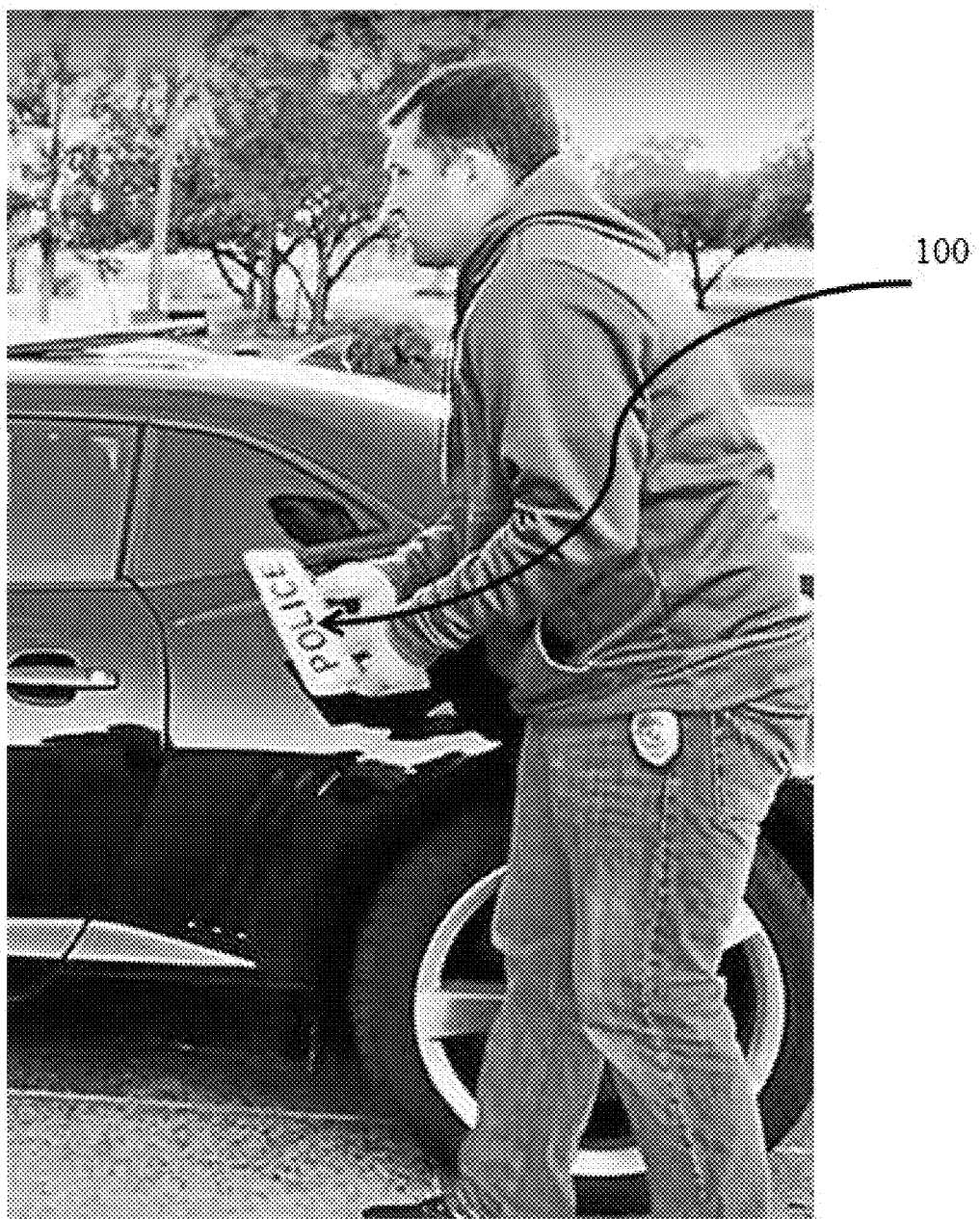

FIG. 9. depicts one manner of use in which a folded arm banner identification safety device of FIG. 1 can be unfolded.

Figure 10:
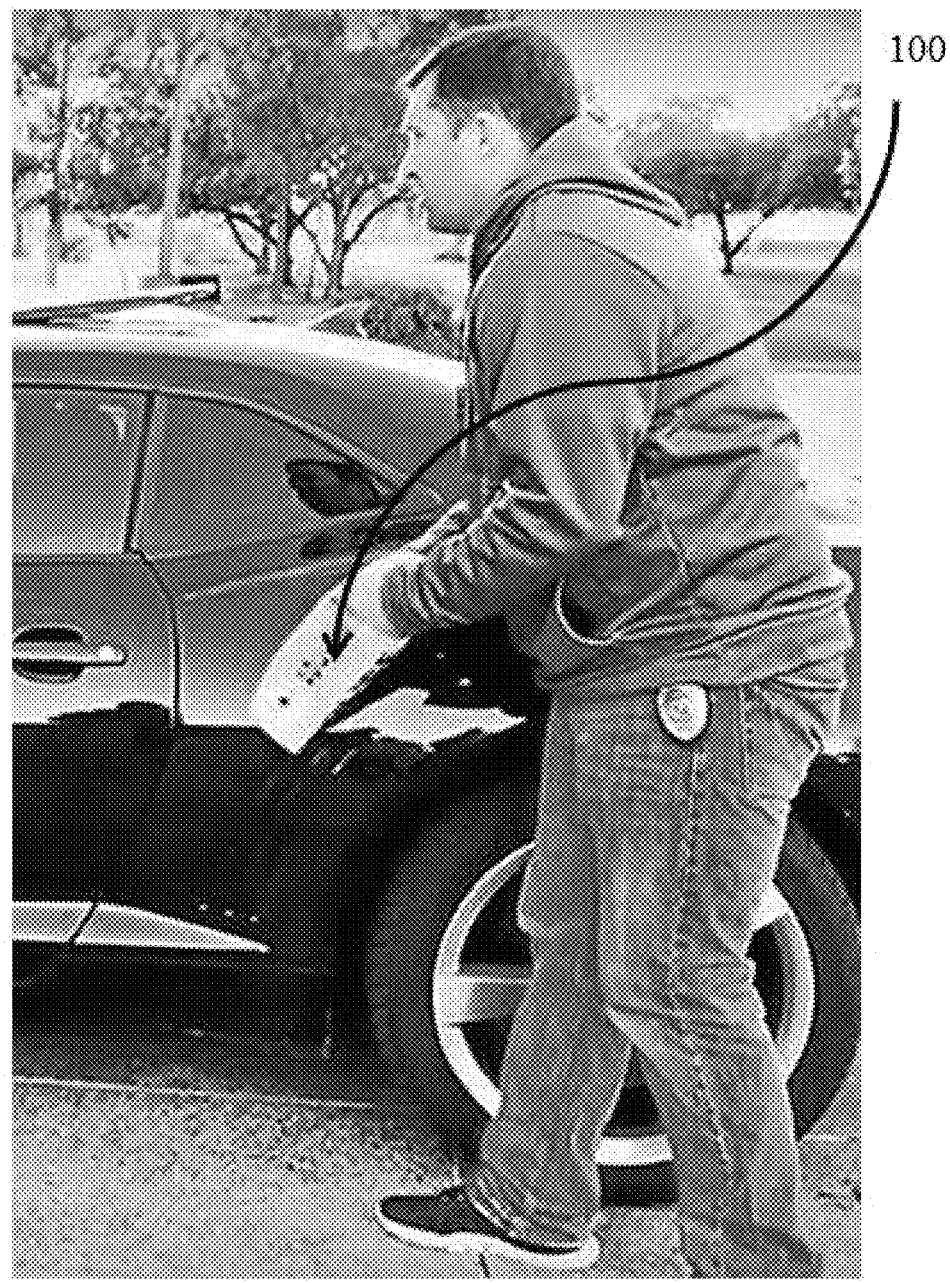

FIG. 10 depicts one manner of use in which an unfolded arm banner identification safety device of FIG. 1 is may be attached by inserting hand into the vertical end.

Figure 11:
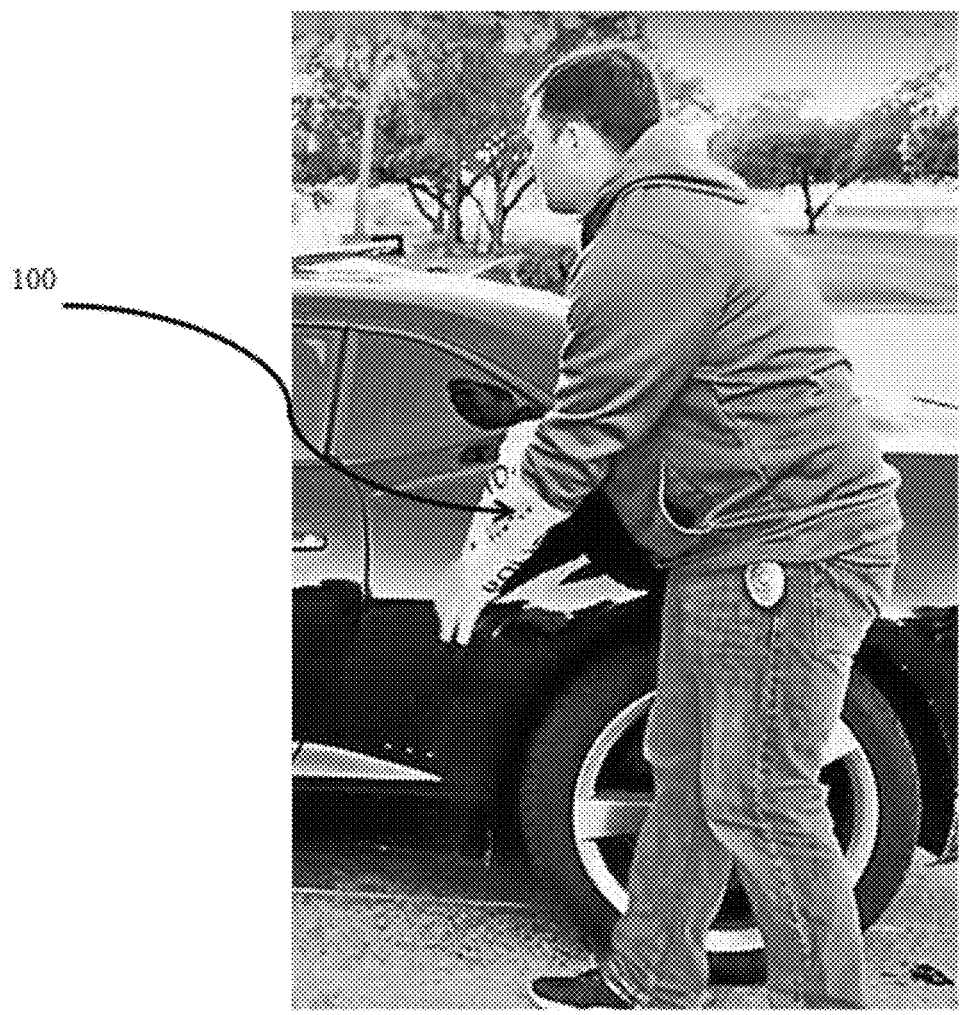

FIG. 11 depicts one manner of use in which an arm banner identification safety device of FIG. 1 is pulled onto the forearm.

Figure 12:
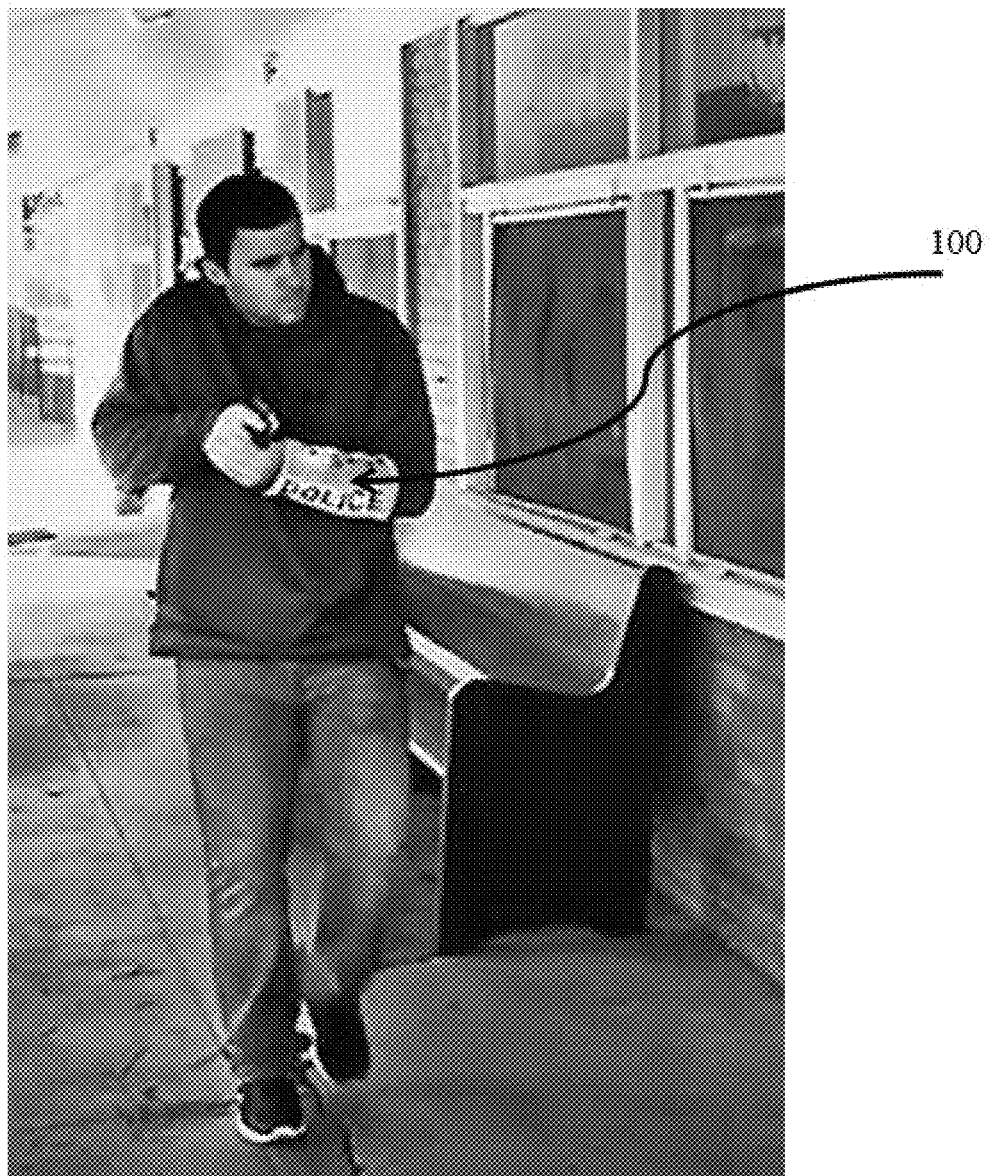

FIG. 12 depicts one manner of use in which an arm banner identification safety device of FIG. 1 can be attached to the forearm of first responders including law enforcement officers such as the plainclothes police officer in this example, emergency medical service providers and firefighters, as well as other individuals licensed or authorized to carry a firearm. Note that the badge of the plainclothes officer in this example is not visible from this angle and without the present invention, the officer could easily be mistaken for an threatening suspect.

Figure 13:

FIG. 13 depicts one manner of use in which an arm banner identification safety device of FIG. 1 is attached to the forearm of first responders including law enforcement officers such as the plainclothes police officer in this example, emergency medical service providers and firefighters, as well as other individuals licensed or authorized to carry a firearm, and can be easily seen by another individual such as the uniformed police officer in this example. Note that the badge of the plainclothes officer in this example is only partially visible from this angle and without the present invention, the officer could easily be mistaken for an threatening suspect.

DETAILED DESCRIPTION OF THE INVENTION

Referring now to the invention in more detail, in FIG. 1 there is shown the method of use of an arm banner identification safety device 100, constructed of a rectangle section of flexible material 110, with reflective material strips 120*a* and 120*b* added on the right and left of the material. Identification wording or lettering 140*a* and 140*b* is added on the reflective material strips 120a and 120b. Additional identification wording or lettering 150 is added in the lower center portion directly to the flexible material 110. An identification symbol 130 could also be added in the upper center portion directly to the flexible material 110. This optional identification symbol 130 reflects the needs of the final user such as, but not limited to, a badge symbol for devices made for a law enforcement officers, a fire cross symbol for devices made for firefighters, a medical star for devices used by emergency medical personnel, etc. The flexible material 110 is sewn with thread 180 and three elastic button-hole straps, hook and loop straps, or other type adjustable straps 160a, 160b, and 160c are attached to the flexible material 110. The three elastic button-hole straps, hook and loop straps, or other type adjustable straps 160a, 160b, and 160c are attached to three buttons, or buckles, or other type connectors 170a, 170b, and 170c.

In more detail, still referring to the invention of FIG. 1, the two vertical sides of the flexible material 110 are connected by the three elastic button-hole straps, hook and loop straps, or other type adjustable straps 160a, 160b, and 160c to the three buttons, or buckles, or other type connectors 170a, 170b, and 170c. This allows the user to adjust the correct size and keep it in place on the forearm regardless of clothing thickness and/or layering. The identification wording or lettering 140a and 140b, which is on top of the reflective material strips 120a and 120b, is situated in a way that it can be easily recognized while the user is in a shooting stance. The optional identification symbol 130 and the additional identification wording or lettering 150 are positioned in a way that the user can raise the arm and be easily recognized from the rear.

The flexible material 110 that is the base material for the arm banner identification safety device 100 is bright and/or in vivid contrast with the reflective material strips 120a and 120b, the optional identification symbol 130, and the identification wording or lettering 140a, 140b, and 150. This allows the arm banner identification safety device 100 to be easily seen in most lighting conditions. It is made to be folded and kept in pocket or purse when not in use. This allows for easy everyday carrying of the arm banner identification safety device 100. The flexible material 110 can be of different types of materials, but should be a durable, yet flexible material that works well with the reflective material strips 120a and 120b, the optional identification symbol 130, and the identification wording or lettering 140a, 140b, and 150.

Figure 2:
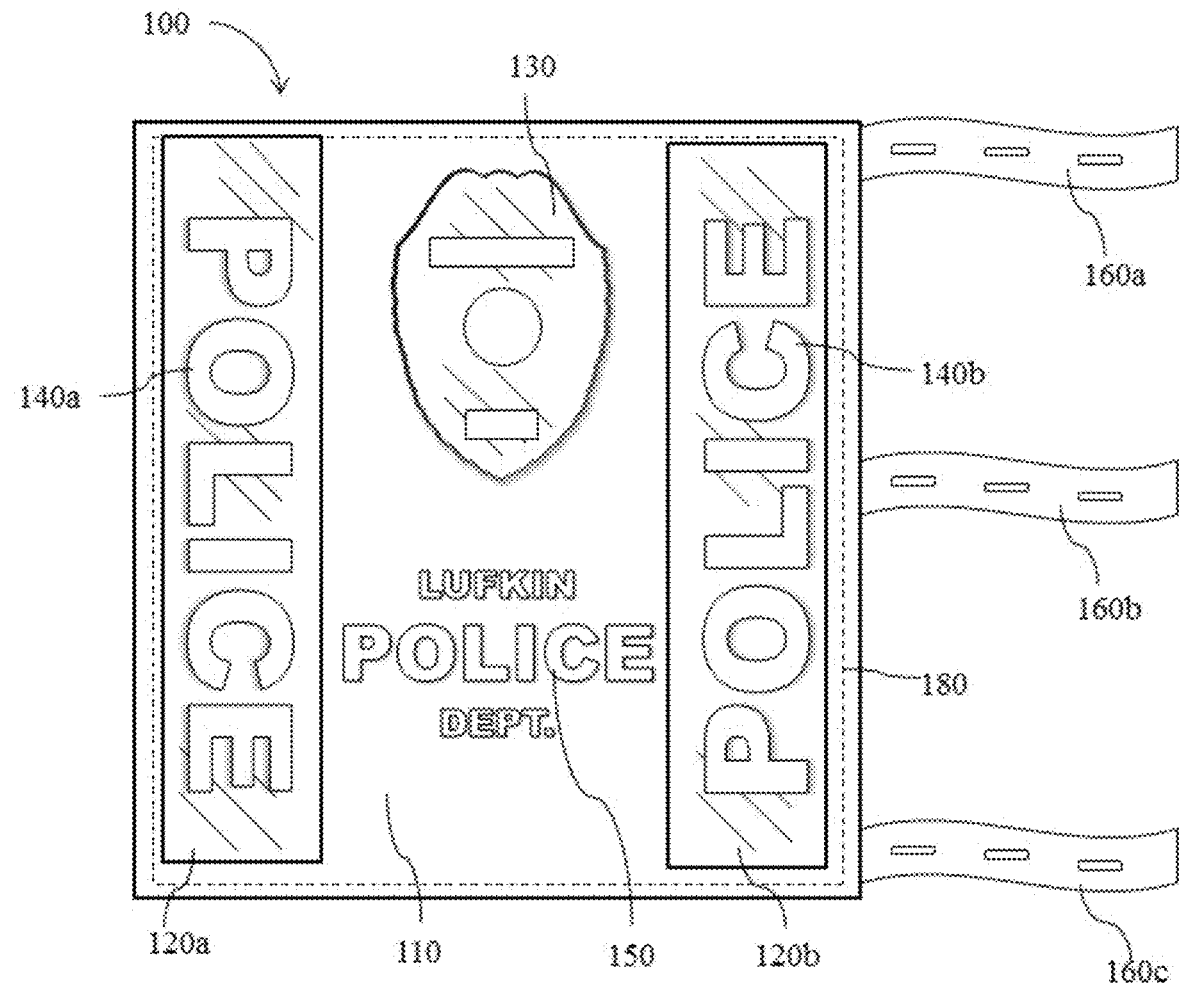
FIG. 2 depicts a top view of the arm banner identification safety device of FIG. 1 with the straps unattached on one side.
Figure 3:
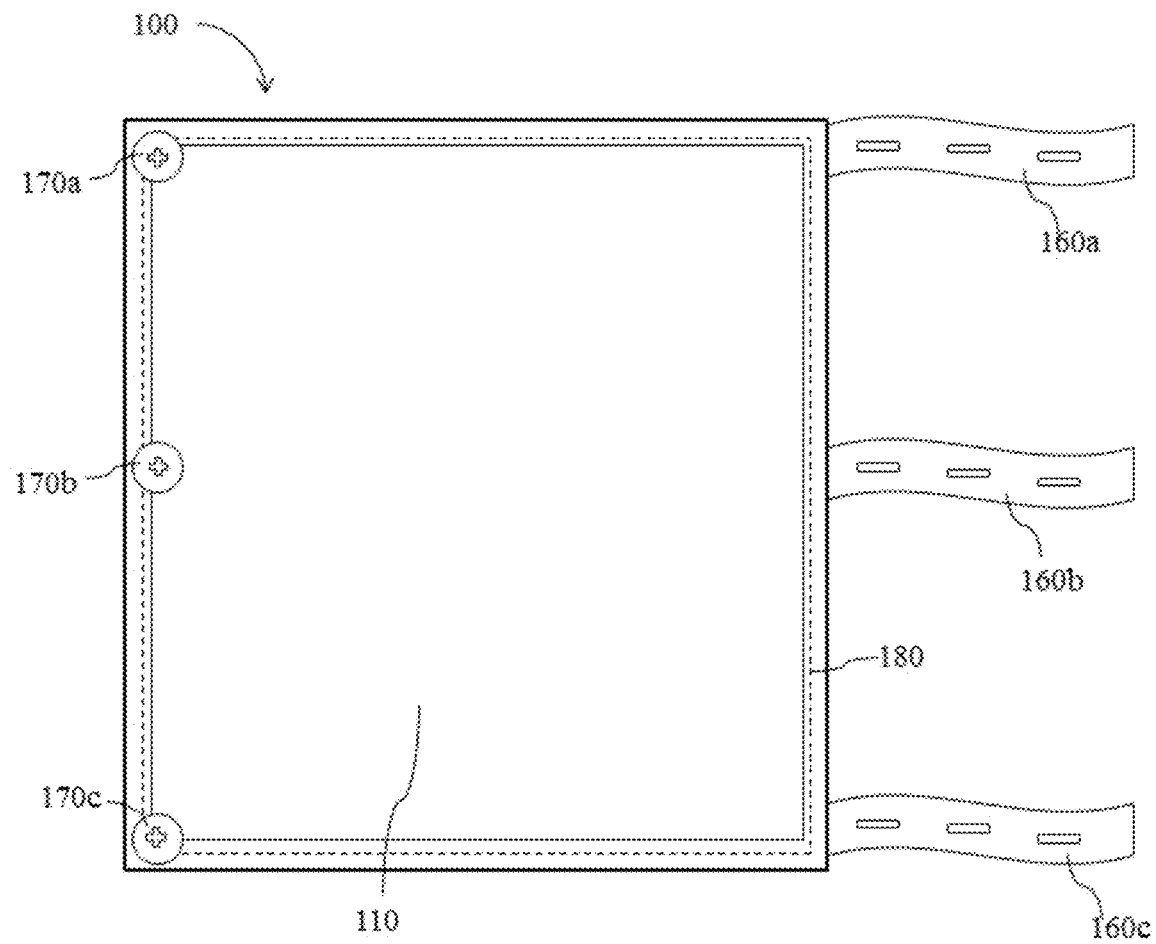
FIG. 3 depicts an under view of the arm banner identification safety device of FIG. 1 with the straps unattached on one side.

Referring now to the invention shown in FIG. 2 there is shown the top view of the arm banner identification safety device 100, constructed of a rectangle section of flexible material 110, with two reflective material strips 120a and 120b added on the right and left of the material. Identification wording or lettering 140a and 140b is added on the reflective material strips 120a and 120b. Additional identification wording or lettering 150 is added in the lower center portion directly to the flexible material 110. An optional identification symbol 130 is also added in the upper center portion directly to the flexible material 110. The flexible material 110 is sewn with thread 180 and three elastic button-hole straps, hook and loop straps, or other type adjustable straps 160a, 160b, and 160c are attached to the flexible material 110. Referring now to the invention shown in FIG. 3 there is shown the under view of the arm banner identification safety device 100, constructed of a rectangle section of flexible material 110, which is sewn with thread 180 and three elastic button-hole straps, hook and loop straps, or other type adjustable straps 160a, 160b, and 160c are attached to the flexible material 110. The three elastic button-hole straps, hook and loop straps, or other type adjustable straps 160a, 160b, and 160c are attached to three buttons, or buckles, or other type connectors 170a, 170b, and 170c.

Figure 4:
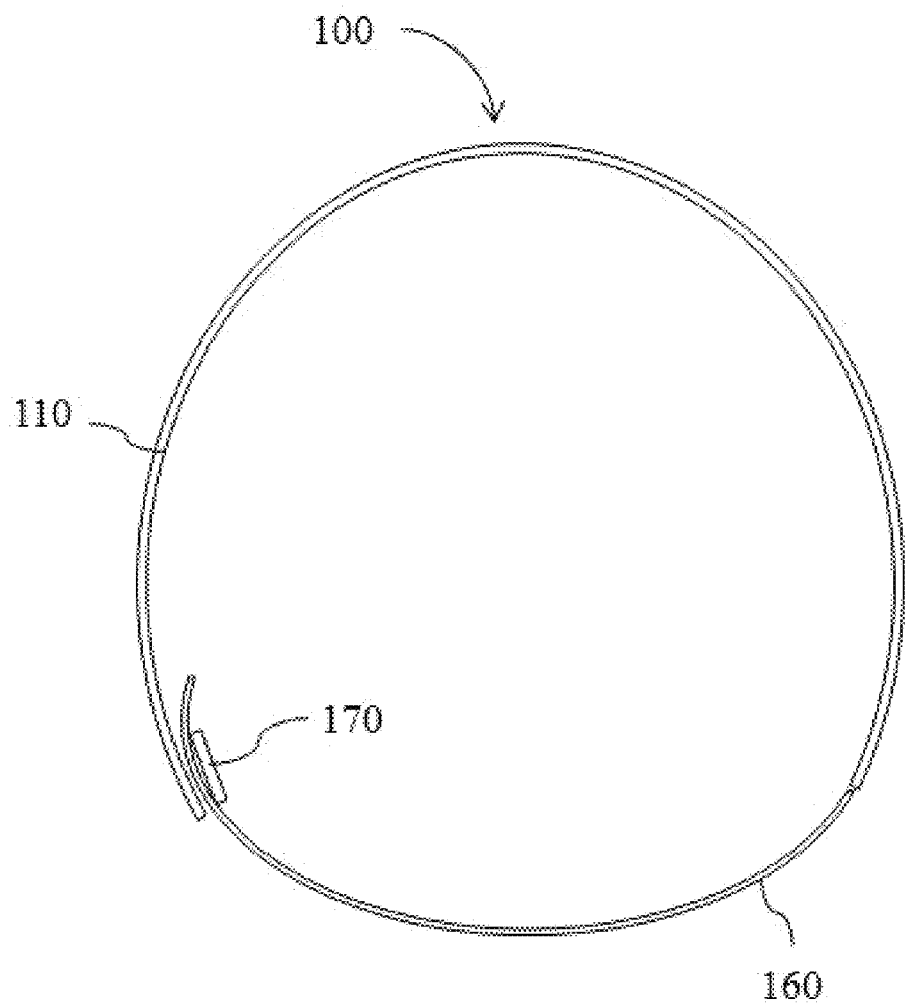
FIG. 4 depicts a side view of the arm banner identification safety device of FIG. 1.
Figure 5:
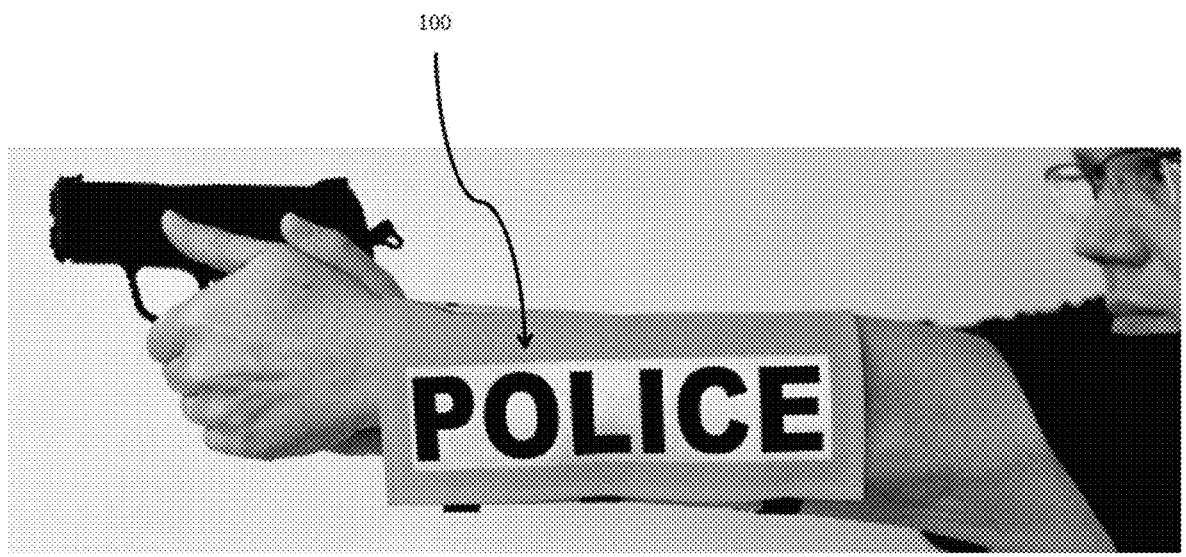
FIG. 5 depicts a horizontal perspective view of an arm banner identification safety device of FIG. 1 being used in one manner.
Figure 6:
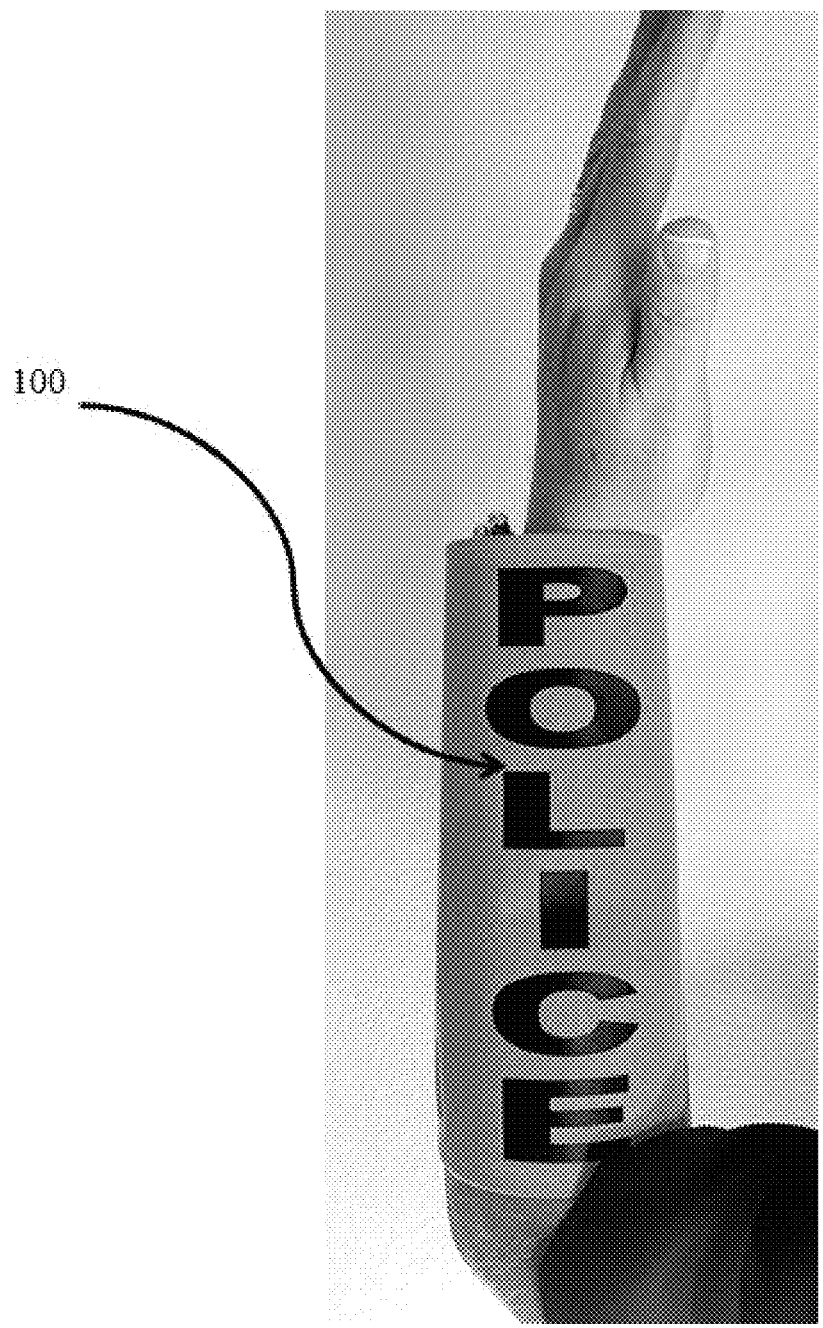
FIG. 6 depicts a vertical perspective view of an arm banner identification safety device of FIG. 1 being used in one manner.
Figure 7:
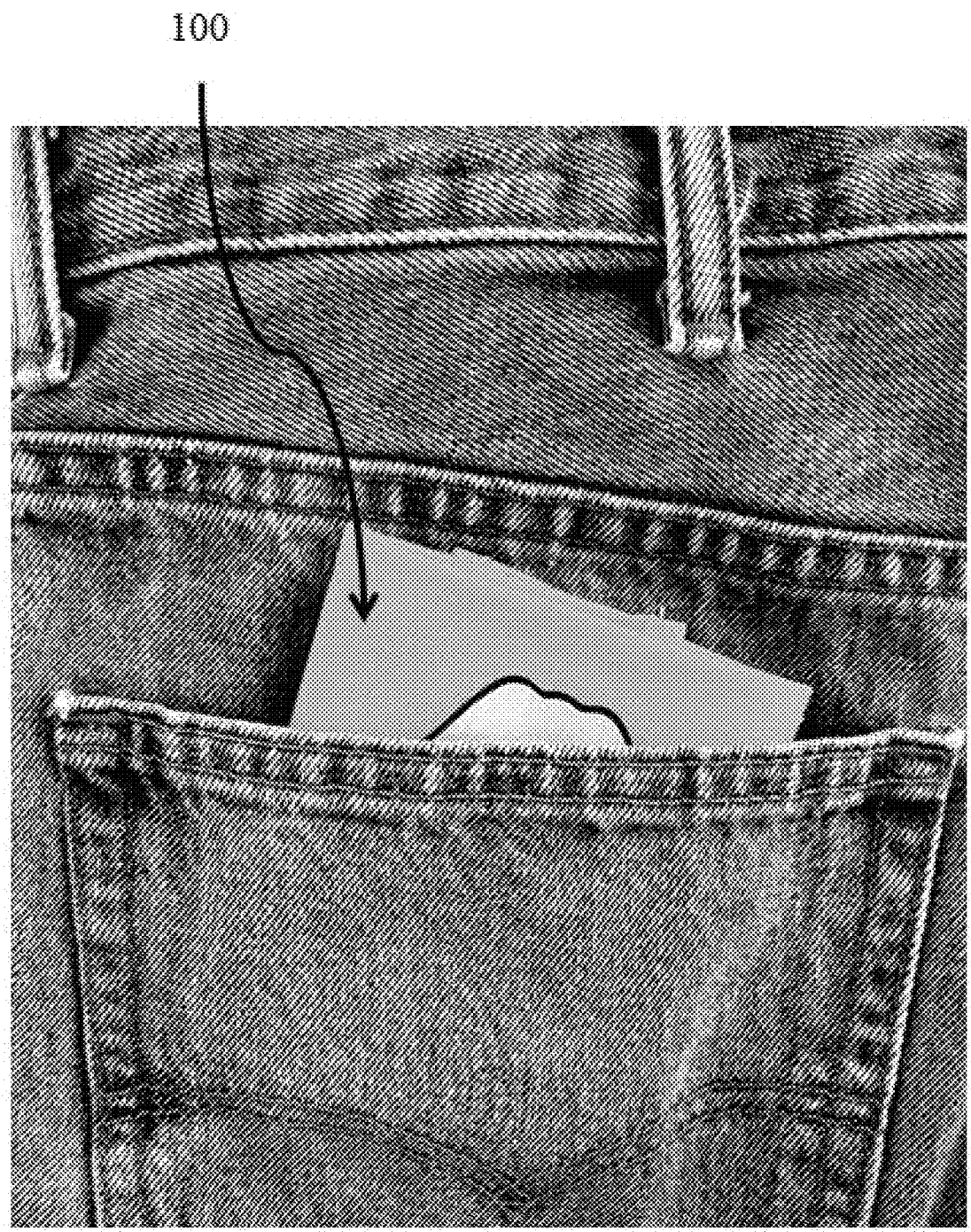
FIG. 7 depicts a folded perspective view and one manner of the carrying of an arm banner identification safety device of FIG. 1.
Figure 8:
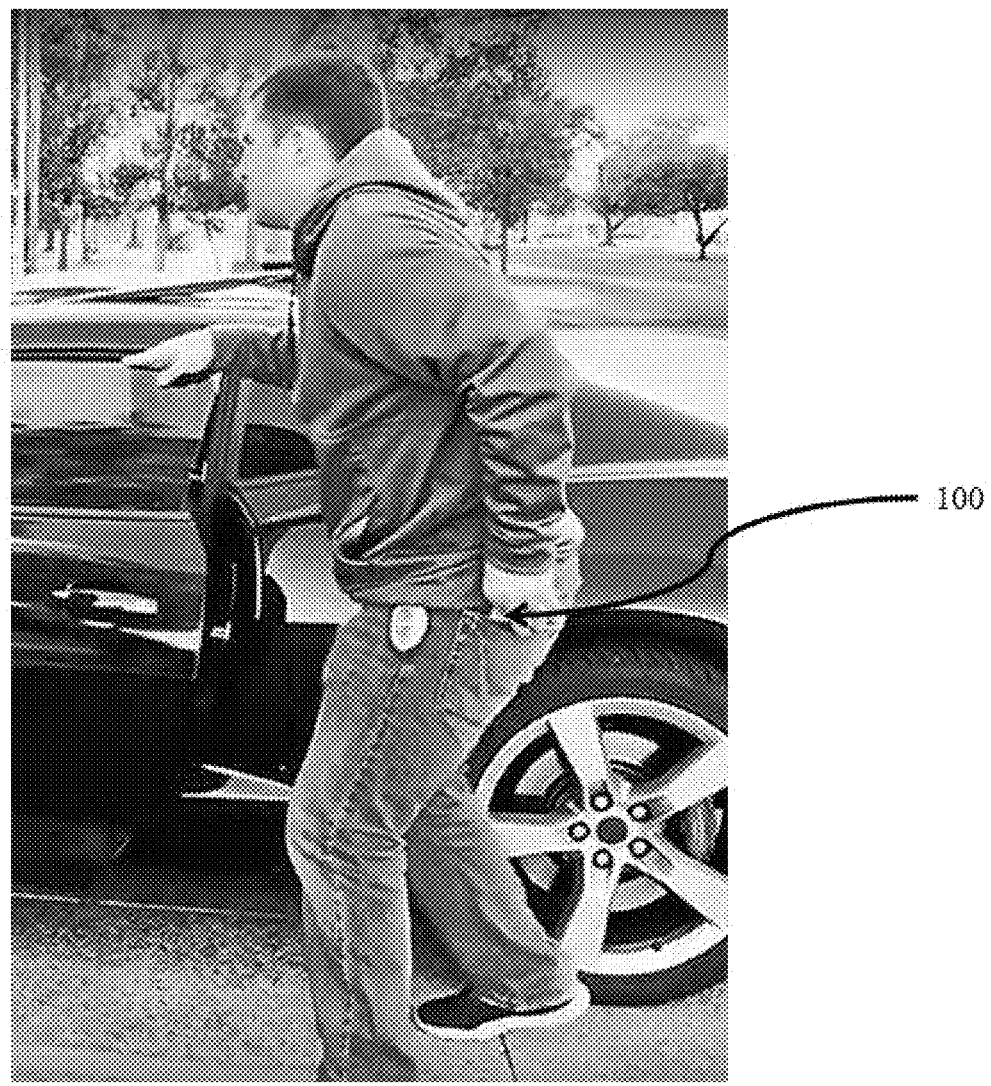
FIG. 8 depicts one manner of use in which a folded arm banner identification safety device of FIG. 1 is carried as in FIG. 7 and can be pulled out by first responders including law enforcement officers such as the plainclothes police officer in this example, emergency medical service providers and firefighters, as well as other individuals licensed or authorized to carry a firearm.

Referring now to the invention shown in FIG. 4 there is shown the side view of the arm banner identification safety device 100, constructed of a rectangle section of flexible material 110, with the first elastic button-hole strap, hook and loop strap, or other type adjustable strap 160a attached to the flexible material 110 and connected to the first button, or buckle, or other type connector 170a.

The advantages of the present invention include, without limitation, that the arm banner identification safety device is highly visible, easily recognized by law enforcement officers and others, small enough for the user to carry in pocket or purse at all times, it is quickly and easily deployed, and does not place a large target on the body. The arm banner safety device is also small enough to be hidden or tucked away if the desire is for it to not be seen.

In broad embodiment, the present invention is a safety device that can be worn on the forearm by first responders including law enforcement officers, emergency medical service providers, firefighters and others, as well as other individuals authorized to carry and/or use a firearm, who are in plainclothes and cannot be identified by uniform. The invention is intended to help prevent accidental shootings of first responders and other non-combatants at emergency incident scenes who are not easily recognized by uniformed law enforcement officers and others. It will also help identify first responders including law enforcement officers, emergency medical service providers, firefighters and others, as well as other individuals authorized to carry and/or use a firearm during non-emergency incidents.

Although the written description and illustration of the present invention contained herein allows one of ordinary skill to make and use what is considered presently to be the best style thereof, those of ordinary skill will understand and appreciate the presence of variations, combinations, and similarities of the specific embodiment and examples herein. The present invention should therefore not be limited by the above described embodiment and examples, but by all embodiments and examples within the scope and spirit of the present invention.

What I claim is:

1. An identification safety device comprising
   a rectangular base made of a flexible material;
   a plurality of light reflective material strips attached to a top surface of the rectangular base, the plurality of light reflective material strips comprising a plurality of identifying words or letters; and
   a plurality of fasteners attached to the rectangular base;
   wherein the identification safety device is characterized by
      a folded condition in which
         the identification safety device is folded and is configured to be carried in a pocket or a purse; and
      an assembled condition in which
         the identification safety device is configured to be worn on a forearm of a wearer; and
   wherein the plurality of fasteners comprises
      a first elastic button strap attached to a first side of the rectangular base;
      a second elastic button strap attached to a first side of the rectangular base;
      a third elastic button strap attached to a first side of the rectangular base;

a first button attached to a bottom surface of the rectangular base;

a second button attached to the bottom surface of the rectangular base; and a third button attached to the bottom surface of the rectangular base.

2. The identification safety device of claim 1, wherein the identification safety device is configured to be used by the wearer selected form the group consisting law enforcement officers, emergency medical service providers, firefighters, persons licensed or authorized to carry firearms, and persons needed to be identified at an emergency scene.

3. The identification safety device of claim 1, wherein the plurality of light reflective material strips comprises a first light reflective material strip; and a second light reflective material strip parallel to the first light reflective material strip.

4. The identification safety device of claim 3, wherein a logo is disposed between the first light reflective material strip and the second light reflective material strip.

5. The identification safety device of claim 1, wherein a first end of the first elastic button strap is between the top surface of the rectangular base and the bottom surface of the rectangular base;

wherein a second end of the first elastic button strap is between the top surface of the rectangular base and the bottom surface of the rectangular base; and wherein a third end of the first elastic button strap is between the top surface of the rectangular base and the bottom surface of the rectangular base.

6. The identification safety device of claim 1, wherein the plurality of light reflective material strips comprises a first light reflective material strip; and a second light reflective material strip parallel to the first light reflective material strip; and wherein a plurality of identifying words, a plurality of identifying letters, or a logo is disposed between the first light reflective material strip and the second light reflective material strip.

\* \* \* \* \*